US00PP35352P2

(12) United States Plant Patent
Zaiger et al.

(10) Patent No.: US PP35,352 P2
(45) Date of Patent: Aug. 29, 2023

(54) INTERSPECIFIC TREE NAMED 'FLAVOR BELLE'

(50) Latin Name: **Interspecific *Prunus***
Varietal Denomination: FLAVOR BELLE

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 200 days.

(21) Appl. No.: 17/300,836

(22) Filed: Nov. 26, 2021

(51) Int. Cl.
*A01H 5/08* (2018.01)
*A01H 6/74* (2018.01)

(52) U.S. Cl.
USPC ..... Plt./180
CPC ..... *A01H 6/7472* (2018.05); *A01H 6/7427* (2018.05)

(58) Field of Classification Search
USPC ..... Plt./180
CPC ..... A01H 5/08; A01H 5/0837
See application file for complete search history.

*Primary Examiner* — Kent L Bell

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree having a vigorous, upright growth habit.
2. Tree being a regular and productive bearer of medium size fruit.
3. Fruit with a high degree of attractive reddish purple skin color.
4. Fruit with very good flavor and eating quality.
5. Fruit with good storage and shipping ability.

1 Drawing Sheet

Botanical designation: Interspecific *Prunus* species.
Variety denomination: 'FLAVOR BELLE'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

Prior varieties:

Among the existing varieties of plum and interspecific trees, which are known to us, and mentioned herein, 'Dapple Supreme' Interspecific (U.S. Plant Pat. No. 16,412) and the proprietary non-patented plum seedling selections '276LF278', '19GF223' and '38RC246' and the proprietary non-patented interspecific seedling selections '139LH28' and '63EG256'.

STATEMENT REGARDING FEDERALLY SPONSORED RESEARCH AND DEVELOPMENT

Not applicable.

ORIGIN OF THE VARIETY

The new and distinct variety of interspecific tree was developed by us in our experimental orchard located near Modesto, Calif. from a first generation cross between our proprietary non-patented plum seedling selection '276LF278' and the interspecific non-patented seedling selection '139LH28'. The seed parent '276LF278' is a first generation seedling from the cross of the non-patented proprietary plum seedling selections '19GF223' and '38RC246'. The pollen parent '139LH28' originated from seed of an open pollinated proprietary non-patented interspecific seedling selection '63EG256'. A large number of these first generation seedlings were planted and grown on their own root system during which time we recognized the desirable tree and fruit characteristics of the present seedling and selected it in 2002 for additional asexual propagation and commercialization.

ASEXUAL REPRODUCTION OF THE VARIETY

In 2002 asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new and distinct variety of interspecific tree is of large size, vigorous, upright growth and a regular and productive bearer of medium size, clingstone fruit with an attractive reddish purple skin color. The fruit is further characterized by its firm yellow flesh, very good flavor and eating quality with good handling and shipping ability. In comparison to its proprietary non-patented plum seed parent '276LF278' the fruit of the new variety is approximately 40 days earlier in maturity. In comparison to its proprietary non-patented interspecific pollen parent '139LH28' the fruit of the new variety is approximately 47 days earlier in maturity. In comparison to the commercial variety 'Dapple Supreme' Interspecific (U.S. Plant Pat. No. 16,412) the fruit of the new variety has yellow flesh compared to red and is approximately 40 days earlier in maturity.

DESCRIPTION OF THE PHOTOGRAPH

The accompanying color photographic illustration shows typical specimens of the foliage and fruit of the present new interspecific variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 19 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 19 year old specimens grown near Modesto, Calif., with color in accordance with Munsell Book of Color published in 1958.

Tree:

*Size*.—Large, pruned to 3 to 3.5 meters in height and width for economical harvesting of fruit. Varies with different cultural practices.

*Vigor*.—Vigorous, tree growth of 1.5 to 2 meters the first growing season. Varies with cultural practices, soil type, fertility and climatic conditions.

*Form*.—Upright growth, usually pruned to vase shape.

*Branching habit*.—Upright, crotch angle approximately 25°, increases with heavy crop load.

*Productivity*.—Productive, thinning and spacing of fruit necessary for desired market size fruit. Number of fruit set varies with climatic conditions during blooming period.

*Bearer*.—Regular, has had adequate fruit set 17 consecutive years. No alternate bearing observed.

*Fertility*.—Self sterile, pollinator required.

*Density*.—Medium dense, usually pruned to vase shape to increase air movement and sunlight to enhance fruit color and health of fruit spurs.

*Hardiness*.—Hardy in all stone fruit growing areas of California. Tree grown in USDA Hardiness Zone 9. Winter chilling requirement approximately 300 hours at or below 45° F.

Trunk:

*Size*.—Medium, average circumference 71.1 cm at 25.4 cm above ground on a 19 year old tree.

*Stocky*.—Medium stocky.

*Texture*.—Medium shaggy, roughness increases with age of tree.

*Color*.—Varies from 10YR 4/2 to 10YR 2/2.

Branches:

*Size*.—Medium. Average circumference 17.8 cm at 1.2 meters above ground. Crotch angle approximately 25°, increases with heavy crop load.

*Surface texture*.—New growth relatively smooth. Mature growth medium rough, roughness increases with age.

*Lenticels*.—Average number 53 in a 25.8 square cm area. Average length 5.0 mm. Average width 1.9 mm. Color varies from 10YR 6/8 to 10YR 4/8.

*Color*.—New growth varies from 5GY 6/6 to 5GY 5/6. Mature growth varies from 10YR 4/2 to 10YR 2/2, varies with age of growth.

Leaves:

*Size*.—Medium. Average length 71.5 mm. Average width 30.6 mm.

*Form*.—Elliptical.

*Apex*.—Acuminate.

*Base*.—Cuneate.

*Margin*.—Serrate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Average length 11.9 mm. Average width 1.2 mm. Longitudinally grooved. Surface — glabrous. Color varies from 5GY 7/6 to 5GY 6/6.

*Glands*.—Type — globose. Size — small. Average length 0.1 mm. Average diameter 0.1 mm. Average number 3, varies from 1 to 4. Located primarily on the upper portion of the petiole and base of leaf blade. Color varies from 5GY 7/6 to 5GY 6/6.

*Stipules*.—None present at time of measurement.

*Color*.—Upper surface varies from 5GY 3/4 to 5GY 3/6. Lower surface varies from 5GY 6/4 to 5GY 4/4. Midvein color varies from 5GY 7/4 to 5GY 7/6.

Flower buds:

*Size*.—Large. Average length 11.2 mm. Average diameter 5.7 mm.

*Hardiness*.—Hardy with respect to California winters.

*Density*.—Dense.

*Form*.—Conical, becoming elongated just before opening.

*Pedicel*.—Average length 8.6 mm. Average width 0.9 mm. Surface — glabrous. Color varies from 2.5GY 6/6 to 2.5GY 6/8.

*Color*.—N 9.5/(white).

*Number of buds per spur*.—Average number 12, varies from 9 to 14.

Flowers:

*Blooming period*.—Date of First Bloom Feb. 8, 2021. Date of Petal Fall Feb. 17, 2021, varies slightly with climatic conditions.

*Size*.—Large. Average height 14.5 mm. Average diameter 19.9 mm.

*Petals*.—Number — normally five, alternately arranged to sepals. Size — large. Average length 13.0 mm. Average width 7.4 mm. Petal apex-rounded. Petal base — truncate. Form — elliptical. Arrangement — free. Margin — sinuate. Both upper and lower surfaces glabrous. Color N 9.5/(white).

*Sepals*.—Number — normally five, alternately arranged to petals. Size — medium to large. Average length 4.4 mm. Average width 3.0 mm. Shape — triangular. Margin — entire. Both upper and lower surfaces glabrous. Color — upper surface varies from 2.5GY 6/6 to 5GY 6/8. Lower surface varies from 2.5GY 6/8 to 5GY 6/6 with 5R 4/8 on edges.

*Stamens*.—Average number per flower 29, varies from 25 to 35. Average filament length 7.3 mm. On average the stamens are below the height of the petals. Filament color N 9.5/(white). Anther color varies from 7.5R 4/12 to 5Y 8/10.

*Pollen*.—Self sterile, pollinator required. Color varies from 2.5Y 7/12 to 5Y 7/12.

*Pistil*.—Number — normally 1, average length 10.7 mm. Position of stigma even with anthers. Surface — glabrous. Color varies from 10Y 8/6 to 10Y 7/6.

*Fragrance*.—Moderate aroma.

*Color*.—N 9.5/(white).

*Pedicel*.—Average length 10.4 mm. Average width 0.9 mm. Surface — glabrous. Color varies from 2.5GY 6/6 to 2.5GY 6/8.

*Number flowers per flower bud*.—Average number 2, varies from 1 to 3.

Fruit:

*Maturity when described*.—Firm ripe and ready for consumption.

*Date of first picking*.—May 20, 2021.

*Date of last picking*.—May 30, 2021, varies slightly with climatic conditions.

*Size*.—Medium. Average diameter axially 50.0 mm. Average transversely in suture plane 55.0 mm. Average weight 100 grams, varies slightly with fertility of the soil, amount of thinning and climatic conditions.

*Form*.—Globose.

*Suture*.—Nearly smooth.

*Ventral surface*.—Smooth.

*Apex*.—Rounded.

*Base*.—Retuse.

*Stem cavity*.—Rounded to slightly elongated in suture plane. Average depth 10.5 mm. Average diameter 7.2 mm.

Stem:

*Size*.—Large. Average length 16.0 mm. Average 1.7 mm.

*Color*.—Varies from 7.5GY 6/6 to 5GY 8/8.

Flesh:

*Ripens*.—Evenly.

*Texture*.—Firm, meaty.

*Fibers*.—Few, small, tender.

*Firmness*.—Firm, comparable to other commercial interspecific varieties.

*Aroma*.—Moderate.

*Amydgalin*.—Undetected.

*Eating quality*.—Very good.

*Flavor*.—Very good, with a good balance between acid and sugar.

*Juice*.—Moderate amount, enhances flavor.

*Acidity*.—Not available.

*Brix*.—Average Brix 17.0°, varies slightly with amount of fruit per tree and climatic conditions.

*Color*.—Varies from 7.5Y 8.5/4 to 10Y 8/8.

*Pit cavity*.—Average length 21.6 mm. Average width 21.1 mm. Average depth 4.7 mm. Color varies from 5Y 5/6 to 7.5Y 6/8.

Skin:

*Thickness*.—Medium.

*Surface*.—Smooth.

*Bloom*.—Moderate amount, complete coverage.

*Tendency to crack*.—None.

*Color*.—Ground color varies from 5R 3/8 to 7.5R 3/12. Overspread with 5R 2/4 to 7.5R 2/8.

*Tenacity*.—Tenacious to the flesh.

*Astringency*.—Slight to none.

Stone:

*Type*.—Clingstone, strong adherence to flesh.

*Size*.—Medium. Average length 22.7 mm. Average width 18.6 mm. Average thickness 8.9 mm.

*Form*.—Ovoid.

*Base*.—Flat.

*Apex*.—Pointed. Average length 1.6 mm.

*Surface*.—Pitted throughout, pits vary from round to elongated.

*Sides*.—Unequal, one side extending slightly further from suture plane.

*Ridges*.—Relatively smooth, extending from base to apex.

*Tendency to split*.—None.

*Color*.—Varies from 7.5YR 6/12 to 7.5YR 5/10.

Kernel:

*Size*.—Medium. Average length 11.1 mm. Average width 9.1 mm. Average depth 5.1 mm.

*Form*.—Ovoid.

*Viability*.—Viable, complete embryo development.

*Skin color*.—Varies from 7.5Y 9/2 to 7.5Y 9/4.

Use: Dessert. Market — local and long distance.

Keeping quality: Good, held firm in cold storage 3 weeks at 38° to 42° F. without shriveling, internal breakdown of flesh or appreciable loss of flavor.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program. No atypical resistances/susceptibilities have been noted under normal cultural practices.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

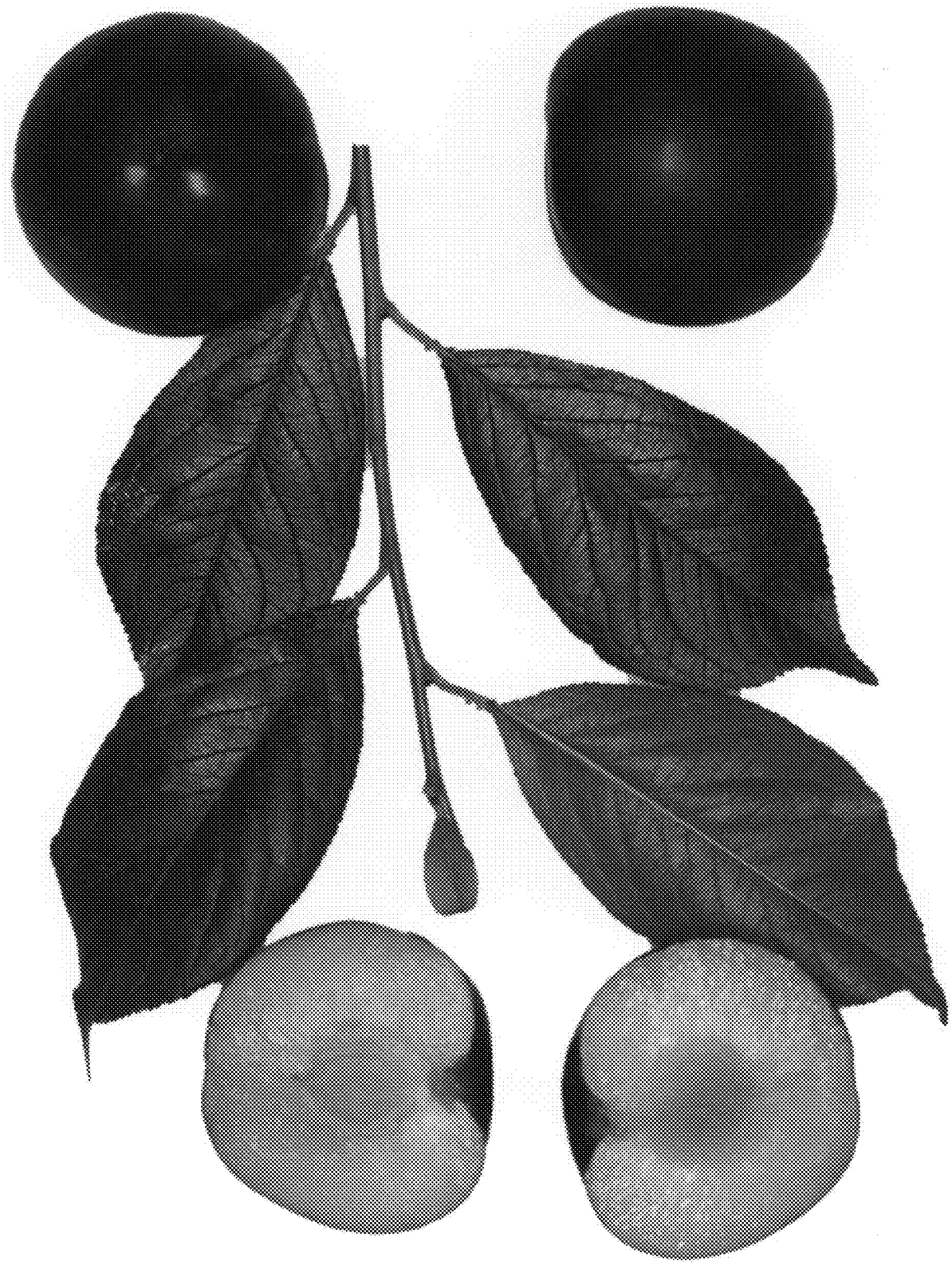

* * * * *